(12) United States Patent
Yang et al.

(10) Patent No.: US 12,178,649 B2
(45) Date of Patent: Dec. 31, 2024

(54) ULTRASONIC DATA PROCESSING METHOD, ULTRASONIC DEVICE AND STORAGE MEDIUM

(71) Applicant: SHENZHEN MINDRAY BIO-MEDICAL ELECTRONICS CO., LTD., Guangdong (CN)

(72) Inventors: Guanghui Yang, Shenzhen (CN); Peiying He, Shenzhen (CN); Huaiqing Gao, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 639 days.

(21) Appl. No.: 17/325,991

(22) Filed: May 20, 2021

(65) Prior Publication Data
US 2021/0353256 A1 Nov. 18, 2021

Related U.S. Application Data

(63) Continuation of application No. PCT/CN2018/117020, filed on Nov. 22, 2018.

(51) Int. Cl.
*A61B 8/00* (2006.01)
*A61B 8/08* (2006.01)
(Continued)

(52) U.S. Cl.
CPC ............... *A61B 8/463* (2013.01); *A61B 8/08* (2013.01); *G01S 7/52074* (2013.01); *G16H 30/20* (2018.01)

(58) Field of Classification Search
CPC .......... A61B 8/463; A61B 8/08; G16H 30/20; G10S 7/52074
(Continued)

(56) References Cited

U.S. PATENT DOCUMENTS

| | | | |
|---|---|---|---|
| 9,402,601 B1 * | 8/2016 | Berger | A61B 8/54 |
| 10,751,030 B2 * | 8/2020 | Kang | A61B 8/5246 |

(Continued)

FOREIGN PATENT DOCUMENTS

| | | |
|---|---|---|
| CN | 101721227 A | 6/2010 |
| CN | 102930170 A | 2/2013 |

(Continued)

OTHER PUBLICATIONS

PCT International Search Report and the Written Opinion mailed Aug. 22, 2019, issued in related International Application No. PCT/CN2018/117020, with partial English translation (10 pages).
(Continued)

*Primary Examiner* — William D Titcomb
(74) *Attorney, Agent, or Firm* — Sheppard Mullin Richter & Hampton LLP

(57) ABSTRACT

An ultrasonic data processing method, said method being applied to an ultrasonic device. Said method comprises: acquiring an ultrasonic image by scanning a target object with an ultrasound probe; acquiring a scanning parameter information of the ultrasound probe; acquiring object information corresponding to the target object; and establishing an association among the object information, the scanning parameter information and the ultrasonic image. Further disclosed are an ultrasonic device and a storage medium.

22 Claims, 10 Drawing Sheets

(51) Int. Cl.
*G01S 7/52* (2006.01)
*G16H 30/20* (2018.01)

(58) Field of Classification Search
USPC .......................................................... 382/128
See application file for complete search history.

(56) References Cited

U.S. PATENT DOCUMENTS

| | | | |
|---|---|---|---|
| 10,987,084 B2* | 4/2021 | Anand | G16H 40/63 |
| 11,564,663 B2* | 1/2023 | Kim | A61B 8/585 |
| 11,717,261 B2* | 8/2023 | Zhao | A61B 8/4405 |
| | | | 248/123.11 |
| 2005/0119569 A1* | 6/2005 | Ohtake | A61B 8/463 |
| | | | 600/437 |
| 2007/0123776 A1 | 5/2007 | Aharoni et al. | |
| 2014/0051984 A1* | 2/2014 | Berger | A61B 18/02 |
| | | | 600/424 |
| 2016/0074015 A1 | 3/2016 | Eda | |
| 2018/0368812 A1* | 12/2018 | Kim | G01S 7/52084 |
| 2019/0383920 A1* | 12/2019 | Kook | G01S 7/52053 |
| 2021/0063554 A1* | 3/2021 | Kook | A61B 8/4477 |
| 2022/0047248 A1* | 2/2022 | Osumi | A61B 8/565 |
| 2022/0308193 A1* | 9/2022 | Kook | A61B 8/4472 |
| 2023/0000465 A1* | 1/2023 | McLaughlin | G06F 3/017 |

FOREIGN PATENT DOCUMENTS

| | | |
|---|---|---|
| CN | 103690191 A | 4/2014 |
| CN | 104622500 A | 5/2015 |
| CN | 108065965 A | 5/2018 |
| KR | 10-2015-0134299 A | 12/2015 |

OTHER PUBLICATIONS

First Search dated Feb. 5, 2024, issued in related Chinese Application No. 201880097251.2 (2 pages).

* cited by examiner

FIG. 9

ULTRASONIC DATA PROCESSING METHOD, ULTRASONIC DEVICE AND STORAGE MEDIUM

This application is a continuation application of International Patent Application No. PCT/CN2018/117020, filed with the China National Intellectual Property Administration (CNIPA) on Nov. 22, 2018. The entire content of the above-referenced application is incorporated herein by reference.

TECHNICAL FIELD

The present disclosure relates to data processing, in particular to an ultrasonic data processing method, an ultrasound device and a storage medium.

BACKGROUND OF THE INVENTION

In the use of an existing ultrasound device, when multiple patients use the same probe for testing, the cross-use of the ultrasound probe is likely to cause cross-infection between the patients. Therefore, it is necessary to record the use of the ultrasound probe to make information related to the use of the ultrasound probe can be traced. However, the use records of an existing ultrasound device often need to be manually recorded by medical personnel during use. Such operational manner is less efficient in recording and querying. Moreover, the records may be in disorder and thus affect the maintenance of records when medical personnel is unskilled.

SUMMARY OF THE INVENTION

The embodiments of the present disclosure can automatically record related information about the use of an ultrasound probe and automatically associate them by providing an ultrasonic data processing method, an ultrasound device, and a storage medium, thereby improving the effectiveness of traceability.

The technical solutions of the embodiments of the present disclosure may be implemented as follows.

In a first aspect, an ultrasonic data processing method applied to an ultrasound device is provided in the present disclosure. The method may include: acquiring an ultrasound image by scanning a target object with an ultrasound probe;
  acquiring a scanning parameter information of the ultrasound probe;
  acquiring an object information corresponding to the target object; and
  establishing an association among the object information, the scanning parameter information and the ultrasound image.

In a second aspect, an ultrasound device configured to perform an ultrasound detection by controlling an ultrasound probe is provided in the present disclosure. The ultrasound device may include:
  an ultrasound probe configured to scan a target object to acquire an ultrasound image;
  a memory configured to store executable instructions; and
  a processor configured to execute the executable instructions stored in the memory to:
  acquire an ultrasound image by scanning the target object with the ultrasound probe;
  acquire a scanning parameter information of the ultrasound probe;
  acquire an object information corresponding to the target object; and
  establish an association among the object information, the scanning parameter information and the ultrasound image.

In a third aspect, the present disclosure provides a storage medium storing executable instructions that, when executed by a processor, cause the processor to implement the method of the first aspect.

With the ultrasonic data processing method, ultrasound device, and storage medium provided in the embodiments of the present disclosure, ultrasound images, scanning parameter information and object information of a target object may be acquired by scanning the target object by the ultrasound probe and an association among the object information, the scanning parameter information and the ultrasound images may be established, so that medical staff can trace the use records of the ultrasound probe in subsequent operations, preventing the safety of patients from being affected by medical staff whose experience is weak, and improving the efficiency of recording and query of ultrasound probe.

BRIEF DESCRIPTION OF THE DRAWINGS

FIG. 9 is a schematic diagram of an optional display interface provided by an embodiment of the present disclosure.

DETAILED DESCRIPTION

Figure 1:
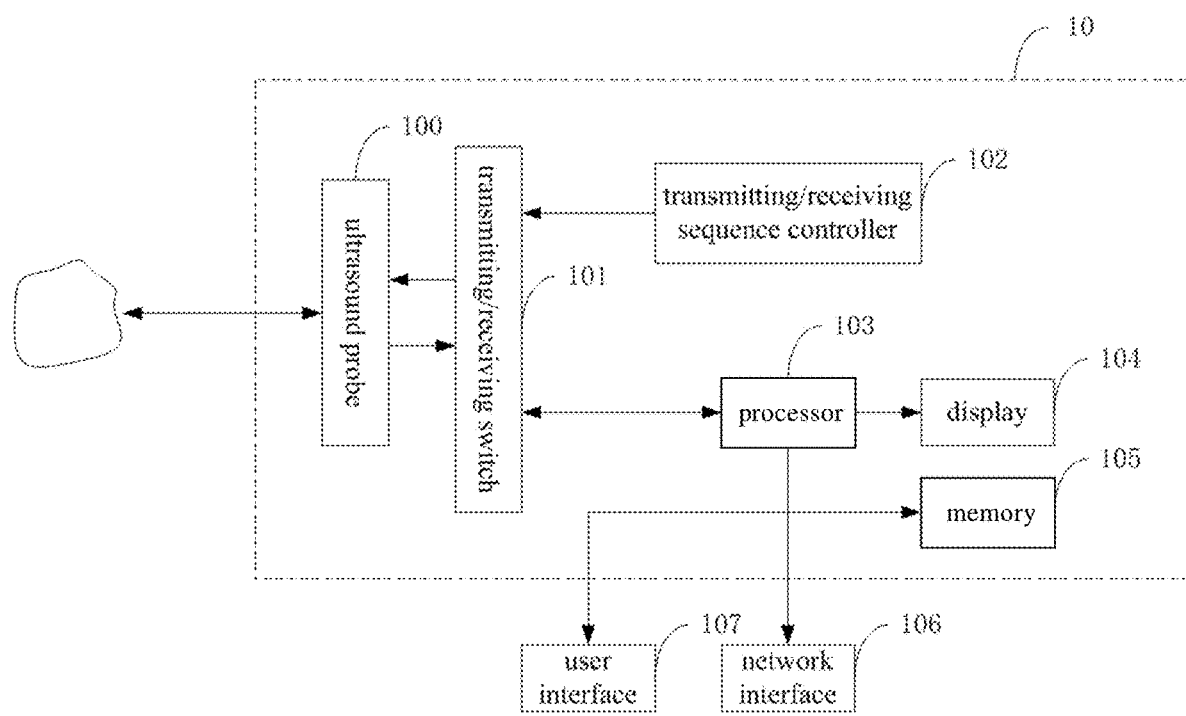
FIG. 1 is a schematically structural block diagram of an ultrasound device in an embodiment of the present disclosure.

In order to make the objectives, technical solutions and advantages of the present disclosure clearer, the present disclosure will be further described in detail below in conjunction with the accompanying drawings. The present disclosure should not be construed as being limited to the provided embodiments; on the contrary, the content described in the embodiments of the present disclosure makes the present disclosure comprehensive and complete, and conveys the concept of the embodiments of the present disclosure to those skilled in the art. Therefore, other embodiments obtained by those skilled in the art without creative work shall fall within the protection scope of the present disclosure.

It should be noted that, in the embodiments of the present disclosure, the terms "comprise", "include" or any other variants thereof are intended to cover non-exclusive inclusion, so that a method or server including a series of elements not only includes elements that are clearly stated, but also includes other elements that are not explicitly listed, or elements inherent to implement the method or server. If there are no more restrictions, the element defined by the sentence "including a . . . " does not exclude the existence of other related elements in the method or processor or memory that includes the element.

It should be noted that in the following description, "an embodiment" is involved to describe a subset of all possible embodiments, but it is understood that "an embodiment" may be the same subset or different subsets of all possible embodiments, and can be combined with each other without conflict.

Before describing the present disclosure in further detail, the terms and phrases involved in the embodiments of the present disclosure will be described. The terms and phrases involved in the embodiments of the present disclosure are applicable to the following explanations.

1) Scanning parameter information, used to represent system parameters involved in the use of the ultrasound device, may include but shall not be limited to:

probe attribute information, including: probe type, probe serial number and so on, where the probe type can be convex-array, linear-array, phased-array, etc. according to its function; the probe type can be classified into an abdominal convex-array probe, an abdominal microconvex-array probe, a cardiac micro-convex-array probe, a transvaginal probe, a transrectal probe, an intraoperative probe, a biplanar intracavitary probes and so on in the light of directions of application; and the probe serial number is used to distinguish different probes of the same type, that is, each probe of the same type has a different serial number from the others, for example, serial number 1, serial number 2, serial number 3 and so on; and probe scanning information, including: scan mode, scan position, scan time and so on; where the scan mode may be B-scan mode, color-flow scan mode, Doppler scan mode and so on; the scan position may be the position of different tissues and organs, for example, the heart, abdomen, fetus and so on; the scan time may be scan-start time, scan-end time, or scanning elapsed time; and the probe scanning information may also naturally include other imaging parameters, such as imaging range, imaging frequency, imaging depth, imaging focus, image gain, dynamic range, sampling gate, wall filtering and so on.

2) Object information, used to represent the relevant information of a target object, may include but shall not be limited to:

object information of the target object, for example, a patient's name, age, gender, occupation, contact details, medical history and so on; and object information of a scanner who scans the target object, for example, a doctor's name, rank, department, etc.

3) "in response to", used to indicate a condition or state on which an executed operation depends. When the dependent condition or state is met, the one or more executed operations may be real-time or be delayed for a set time; unless otherwise specified, there is no restriction on the order of execution of the operations.

FIG. 1 is a schematically structural block diagram of an ultrasound device 10 in an embodiment of the present disclosure. The ultrasound device may be a portable ultrasound device, a desktop ultrasound device and so on. The ultrasound device 10 may include an ultrasound probe 100, a transmitting/receiving switch 101, a transmitting/receiving sequence controller 102, a processor 103, and a display 104. The transmitting/receiving sequence controller 102 may excite the ultrasound probe 100 through the transmitting/receiving switch 101 to transmit ultrasonic waves to the target object, and may also control the ultrasound probe 100 to receive ultrasonic echoes returned from the target object to obtain ultrasonic echoes/data. The processor 103 may process the ultrasonic echoes/data to obtain relevant parameters and ultrasound images of the target object. The ultrasound images obtained by the processor 103 may be stored in a memory 105, and be displayed on the display 104.

In an embodiment of the present disclosure, the aforementioned processor 103 of the ultrasound device 10 can be implemented by hardware. Circuits, single or multiple application specific integrated circuits (ASICs), single or multiple general integrated circuits, single or multiple microprocessors, single or multiple programmable logic devices, or the combination of the aforementioned circuits or devices, or other suitable circuits or devices may be adopted, so that the processor 103 can execute the corresponding steps of the ultrasonic data processing method in the following various embodiments.

In an embodiment of the present disclosure, the display 104 of the ultrasound device 10 may be a touch screen, a liquid crystal display, etc., or a display device independent of the ultrasound device 10 (such as a liquid crystal display, a TV, etc.), or a display screen on electronic devices such as mobile phones and tablets.

In an embodiment of the present disclosure, the memory 105 of the ultrasound device 10 may be a flash memory card, a solid state memory, a hard disk, and the like.

As shown in FIG. 1, the ultrasound device 10 may further include: at least one network interface 106 and a user interface 107. The components in the ultrasound device 100 may be coupled together via a system bus. It may be understood that the system bus is used to realize the connection and communication between these components. In addition to a data bus, the system bus may also include a power bus, a control bus and a status signal bus, which may be employed according to actual needs.

The user interface 107 may be configured to connect a keyboard, a mouse, a trackball, a touch panel, or a touch screen. The network interface 106 may be configured to connect to wired and wireless networks, and is not specifically limited here.

A computer-readable storage medium applied to the ultrasound device may be provided in an embodiment of the present disclosure. The computer-readable storage medium may store one or more programs which may be executed by one or more processors so as to realize part or all or any combination of the steps in the ultrasonic data processing in the following embodiments of the present disclosure. The computer-readable storage medium may be various media that can store program codes, including: ferromagnetic random access memory (FRAM), read only memory (ROM), programmable read-only memory (PROM), erasable programmable read-only memory (EPROM), electrically erasable programmable read-only memory (EEPROM), flash memory, magnetic surface storage, optical disc(s) or compact disc read-only memory, which may not be limited in the embodiments herein.

In an embodiment of the present disclosure, the processor 103 may be further configured to perform the following steps:

acquiring an ultrasound image by scanning the target object with the ultrasound probe when running the executable instruction stored in the memory; acquiring the scanning parameter information of the ultrasound probe scanning the target object; acquiring the object information corresponding to the target object; and establishing an association among the object information, the scanning parameter information and the ultrasound image.

In an embodiment of the present disclosure, the memory 105 may be configured to store the object information, the scanning parameter information, the ultrasound image and the association; thereby achieving local storage of the object information, the scanning parameter information, the ultrasound image, and the association.

In an embodiment of the present disclosure, the processor 103 may be further configured to perform the following steps: acquiring a storage identifier of the object information, the scanning parameter information, the ultrasound image, and the association. The storage identifier represents the storage state and storage location of the object information, the scanning parameter information, the ultrasound image and the association.

In an embodiment of the present disclosure, the display 104 may also be configured to display at least one of the object information, the scanning parameter information and the ultrasound image.

In an embodiment of the present disclosure, the display 104 may also be configured to display at least one of the object information, the scanning parameter information and the ultrasound image in at least one of a text, a graphic and a voice.

In an embodiment of the present disclosure, the processor 103 may be further configured to perform the following operations:

monitoring the ultrasound probe; and reading the scanning parameter information when the ultrasound probe is activated.

In an embodiment of the present disclosure, the processor 103 may be further configured to perform the following operations:

receiving a notification sent by the ultrasound probe, the notification representing that the ultrasound probe is activated; and in response to the notification, receiving the scanning parameter information send by the ultrasound probe.

In an embodiment of the present disclosure, the processor 103 may also be configured to acquire a usage information of the ultrasound probe; and the display 104 may also be configured to display a warning message and mark an alarm for the ultrasound probe.

In the foregoing embodiments, the scanning parameter information may include at least one of a probe type, a probe serial number, a scan mode, a scan location and a scan time.

In an embodiment of the present disclosure, when the scanning parameter information is the probe serial number:

the processor 103 may be configured to acquire the probe serial number from the ultrasound probe; or the processor may be configured to receive an input for the probe serial number, and acquire the probe serial number according to the input; or the processor may be configured to acquire the probe serial number from a local memory.

Figure 2:
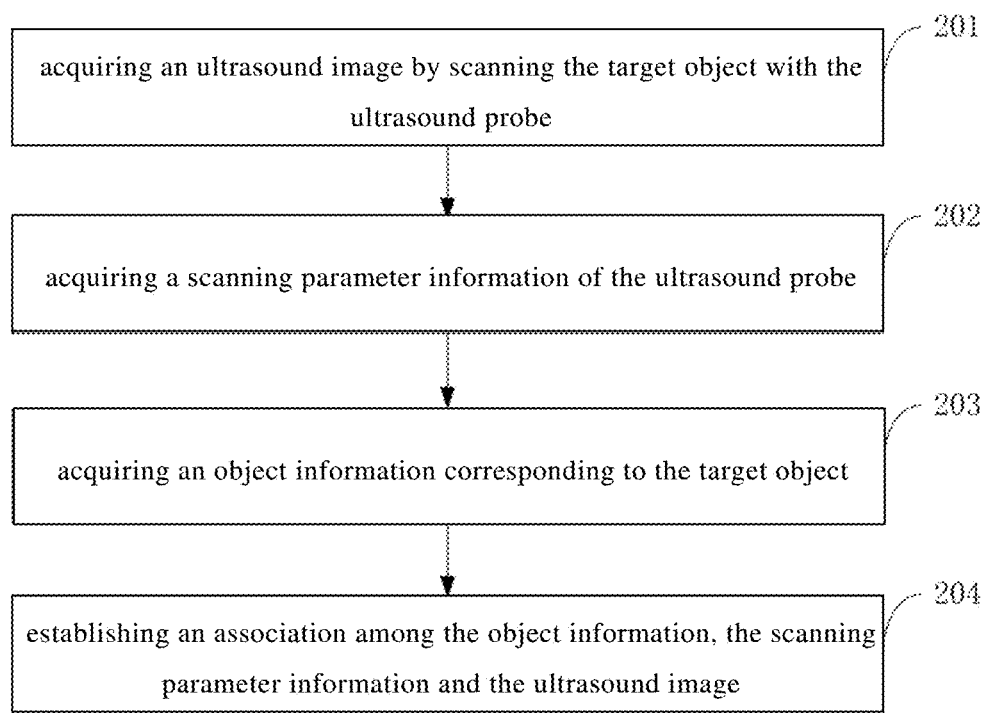
FIG. 2 is a schematic diagram of an optional flow of an ultrasonic data processing method provided by an embodiment of the present disclosure.

The ultrasonic data processing method of the present disclosure may be described below in details. Referring to FIG. 2 shown an optional flowchart of the ultrasonic data processing method provided in an embodiment of the present disclosure, the method may include but not be limited to ultrasound volume imaging, ultrasound planar imaging, etc. This method applied to ultrasound device 10 may include the following detailed process.

Step 201: acquiring an ultrasound image by scanning the target object with the ultrasound probe.

In an embodiment of the present disclosure, the target object involved may be a human or an animal. The ultrasound probe may scan tissues and organs of the human or animal to acquire an ultrasound image of the tissues and organs of the human or animal. For example, when the target object is a person, one or more tissues and organs of the person may be scanned by the ultrasound probe to obtain one or more ultrasound images that correspond to the one or more tissues and organs, thereby performing diagnostic analysis based on the obtained ultrasound images. In practice, the ultrasound images may be a two-dimensional ultrasound image, a three-dimensional ultrasound image, and so on.

In an embodiment of the present disclosure, the transmitting/receiving sequence controller 102 may be used to control the ultrasound probe 100 to transmit ultrasonic waves to the target object through the transmitting/receiving switch 101, control the ultrasound probe 100 to receive the ultrasonic echoes returned from the target object to acquire ultrasonic echo signals/data, and determine the ultrasound images of the target object based on the ultrasonic echo signals/data.

Step 202: acquiring a scanning parameter information of the ultrasound probe.

In an embodiment of the present disclosure, the scanning parameter information may represent the system parameters involved in the use of the ultrasound device, including but not limited to: probe type, probe serial number, scan mode, scan position, scan time, etc. The probe type, such as a linear array probe or a convex array probe, may be acquired directly by the ultrasound probe of the ultrasound device. Certainly, the probe type may be acquired by an input instruction inputted by a user through an interface. Similarly, the scan mode, the scan position and so on may be acquired by the ultrasound device in the aforesaid ways. For example, the scan mode and the scan position may need to be set on the device before ultrasound imaging, that is, information including the scan mode and the scan position may be directly acquired by the ultrasound device via the user's input. The scan mode may be various imaging modes, such as grayscale (B) scan mode, color-flow (C) scan mode, Doppler (D) scan mode. Of course, the scan mode may be other scan modes other than B-scan mode, C-scan mode, and D-scan mode, such as elasticity scan mode, etc., which are not specifically limited here. Moreover, the D-scan mode may be, for example, any one of spectral Doppler scan mode, pulse Doppler scan mode and continuous wave Doppler scan mode, which may not be specifically limited herein. The scan position may be a position corresponding to various tissues and organs of humans or animals. During scanning, the ultrasound device may automatically record relevant time information according to the start time and end time of the scan; of course the time information may also be acquired in other possible ways, which may not be specifically limited herein. Of course, the probe scanning information may also include other imaging parameters, such as imaging range, imaging frequency, imaging depth, imaging focus, image gain, dynamic range, sampling gate, wall filtering and so on. Different scan modes may correspond to different imaging parameters. For example, in the B-scan mode, the imaging parameter information may correspondingly be imaging depth, imaging focus, imaging frequency, dynamic range, magnification, image gain and other parameters. In the C-scan mode, the imaging parameters may be imaging focus, the scale of velocity, imaging frequency, wall filtering, image gain, etc. In the pulse Doppler mode, the imaging parameters may be sampling gate, the scale of velocity, imaging frequency, wall filtering, etc. Of course, the imaging parameters may also be other parameters, such as grayscale, brightness, contrast, etc., which are not specifically limited here.

In practice, when the scanning parameter information is the probe serial number, the probe serial number may be acquired by the ultrasound probe of the ultrasound device, that is, the probe serial number may be stored in a memory chip of the ultrasound probe, or the probe serial number may be fixed on a corresponding ultrasound probe in the manner of firmware; further, the probe serial number may be acquired by the ultrasound probe of the ultrasound device. Alternatively, the ultrasound device may receive an input instruction to the probe serial number, and obtain the probe serial number according to the input instruction, that is, the probe serial number may be acquired by human input via human-computer interaction. Alternatively, the ultrasound device may acquire the probe serial number directly from the local memory, that is, the ultrasound device may obtain the probe serial number before, and store it locally, so that it can be obtained directly locally.

In an embodiment of the present disclosure, the step of acquiring the scanning parameter information of the ultrasound probe scanning the target object may include monitoring the ultrasound probe; and reading the scanning parameter information when the ultrasound probe is activated. In a case of the ultrasound device including a plurality of ultrasound probes, by monitoring the plurality of ultrasound probes, when one ultrasound probe is activated, the ultrasound device can automatically start recording the scanning parameter information corresponding to the use of the ultrasound device so as to completely record the working process of the ultrasound device.

In an embodiment of the present disclosure, the step of acquiring the scanning parameter information of the ultrasound probe scanning the target object may include receiving a notification sent by the ultrasound probe, the notification being used to represent that the ultrasound probe is activated; and in response to the notification, receiving the scanning parameter information sent by the ultrasound probe. When the ultrasound device is equipped with a plurality of ultrasound probes, the ultrasound probe can, through a built-in communication component, the notification, send a notification which may carry the scanning parameter information of the current ultrasound probe.

Further, monitoring ultrasound probe to realize recording the scanning parameter information may be adopted as a main mode of the ultrasound device; and receiving the notification sent by the ultrasound probe to realize recording the scanning parameter information may be adopted as a standby mode of the ultrasound device. When the main mode fails, it can be switched to the standby mode according to a control instruction inputted via the human-computer interaction or a preset operational process, so that the working process of the ultrasound device can be recorded to prevent the failure of the mode from affecting the work of the ultrasound device.

In an embodiment of the present disclosure, the human-computer interaction may be implemented in the following manners:

connecting a mouse to the user interface of the ultrasound device 10 (shown in FIG. 1), and clicking a scan setting button with the mouse so that a scan setting instruction may be received by the processor 103 of the ultrasound device 10. Of course, the processor 103 in the ultrasound device 10 may also be triggered to receive the scan setting instruction in other ways, for example, a touch action like sliding, rotating, etc., or voice input control, which may not be specifically limited herein.

Step 203: acquiring an object information corresponding to the target object.

The object information may represent relevant information corresponding to the target object, including but not limited to: object information of the target object and object information of a scanner who scans the target object. The object information of the target object may include a patient's name, age, gender, occupation, contact details, medical history, etc. The object information of a scanner who scans the target object may be a doctor's name, rank, department, etc., which may be not specifically limited herein.

In an embodiment of the present disclosure, the object information may be acquired by the input by a doctor, or it may be acquired by calling related information stored in a local server or other cloud server by the ultrasound device.

It should be noted that steps 101-103 may be executed unlimited in order, and they may be parallel executed.

Step 204: establishing an association among the object information, the scanning parameter information and the ultrasound image.

By establishing an association among the object information, the scanning parameter information and the ultrasound image, during the process of information traceback, other related information may be traced according to at least one of the object information, the scanning parameter information and the ultrasound image.

Figure 6:
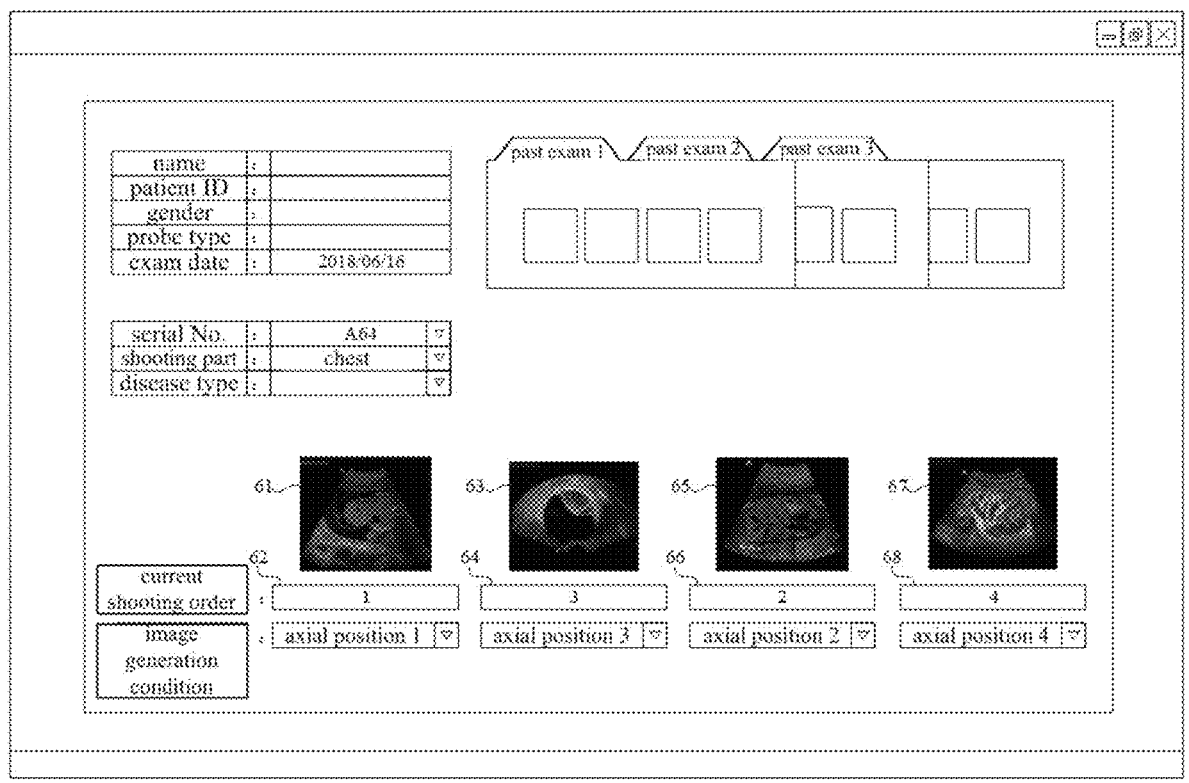
FIG. 6 is a schematic diagram of an optional display interface provided by an embodiment of the present disclosure.

In an embodiment of the present disclosure, ultrasound detection may be performed on different tissues of the same patient with steps 201 to 204. FIG. 6 is a schematic diagram of an optional display interface provided by an embodiment of the present disclosure. In the figure, reference sign 61 may refer to detection of liver combined with ascites, reference sign 63 may refer to high-resolution renal blood flow detection, reference sign 65 may refer to detection of fetal aortic blood flow, and reference sign 67 may refer to detection of umbilical cord blood flow. With the display interface shown in FIG. 6, we may know the scanning parameter information of the ultrasound device currently being used for detecting, including information of the probe type, probe serial number and probe axial position. At the same time, object information may also be gotten, including name, patient Identification (ID, which may be at least one of the patient's ID card number, employee number and examination number), gender, examination date, shooting parts, disease information, and ultrasound images taken in the past examination included in the patient's examination history.

Figure 3:
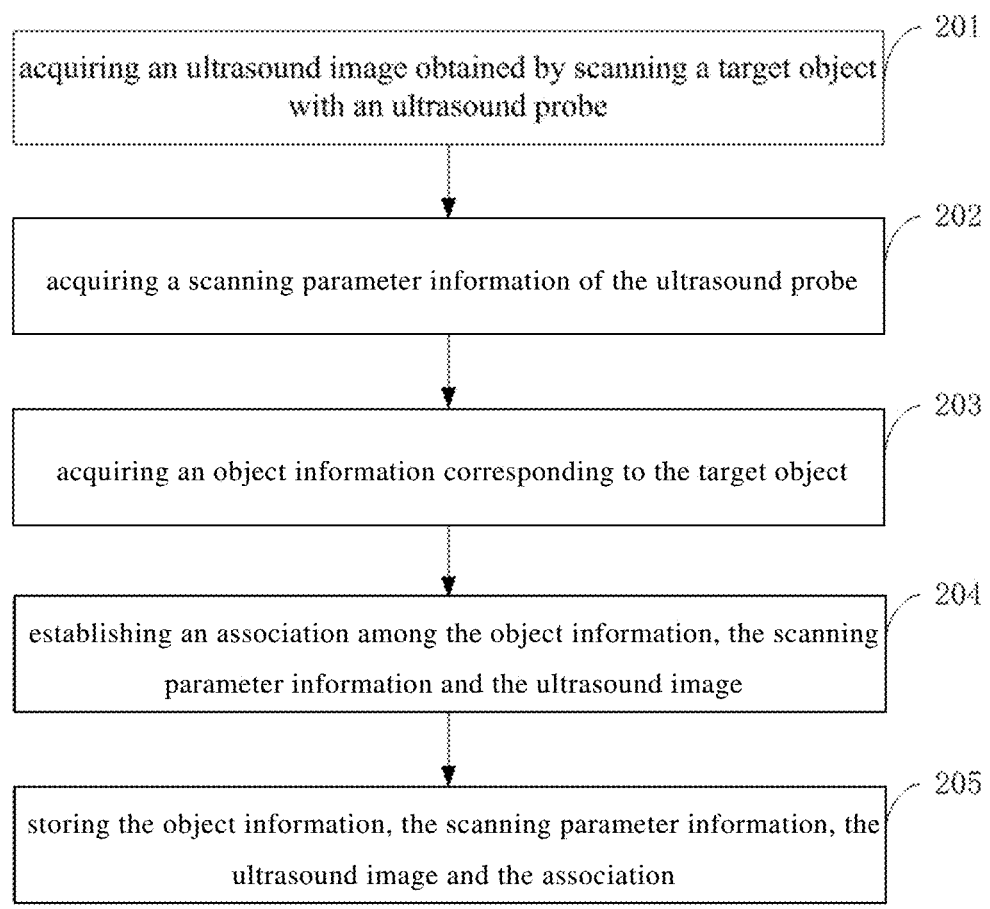
FIG. 3 is a schematic diagram of an optional flow of an ultrasonic data processing method provided by an embodiment of the present disclosure.

Further, as shown in FIG. 3, after step 204, the ultrasonic data processing method provided in the embodiment of the present disclosure may further include:

Step 205: storing the object information, the scanning parameter information, the ultrasound image and the association.

By storing the object information, the scanning parameter information, the ultrasound image, and the association, relevant information can be inquired in time during the process of information traceback.

In this respect, the object information, the scanning parameter information, the ultrasound image, and the association may be stored in local storage, or local server storage, or other cloud server storage, which is not specifically limited herein. After the above-mentioned related information is stored, the storage identifier thereof may be obtained, which represents the storage state and storage location of the above-mentioned related information.

In one possible implementation: the object information, the scanning parameter information, the ultrasound image, and the association may be sent to the server; the storage identifier sent by the server and configured for characterizing the storage state and storage location of the object information, the scanning parameter information, the ultrasound image and the association in the server may be received. It can be seen that after the object information, the scanning parameter information, the ultrasound image, and the association are established, the object information, the scanning parameter information, the ultrasound image, and the association may be sent to a corresponding local server to be stored; thus the data of a plurality of ultrasound devices may be centrally stored and backed up with the local server. Further, the server may also be a cloud server; in this respect, by means of storing the object information, the scanning parameter information, the ultrasound image, and the association established by the ultrasound device in a corresponding cloud server, the object information, the scanning parameter information, the ultrasound image, and the association may be stored remotely, and the equipment provider of the ultrasound device, meanwhile, may also acquire the use status of the ultrasound device, and replace and adjust the ultrasound device in time.

In an embodiment of the present disclosure, it may further include receiving a first display instruction for the ultrasound image, and displaying the ultrasound image according to the first display instruction; or, receiving a second display instruction for the object information, and displaying the object information according to the second display instruction; or, receiving a third display instruction for the scanning parameter information, and displaying the scanning parameter information according to the third display instruction.

It can be seen that, different display instructions generated by human-computer interaction can output different information corresponding to the display instructions via the ultrasound device, so that the information to be outputted may be selected by a user according to different service environment.

Figure 7:
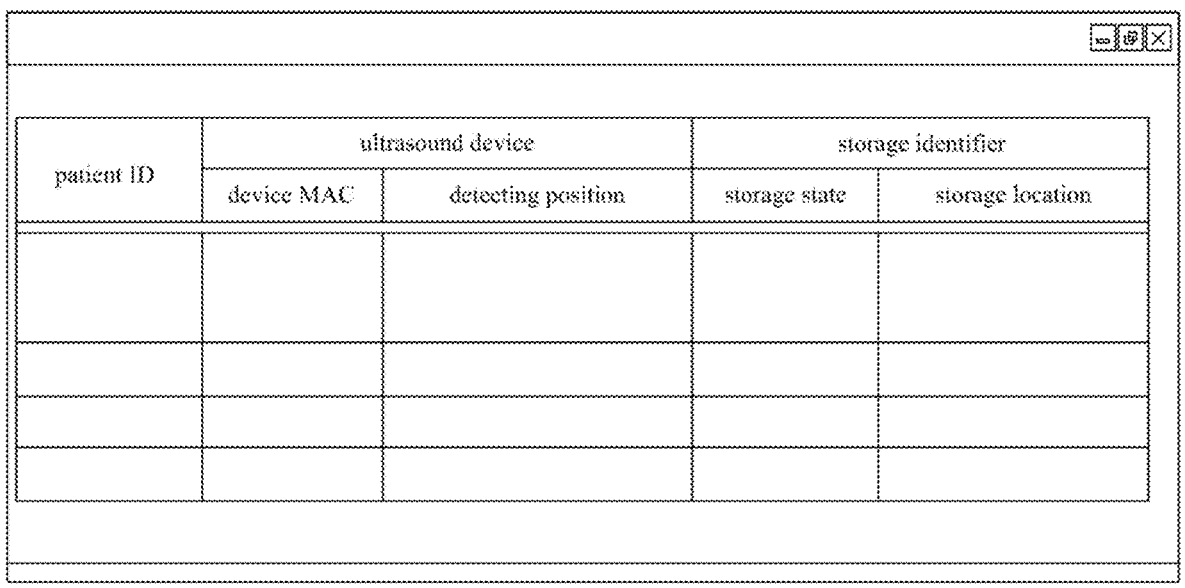
FIG. 7 is a schematic diagram of an optional display interface provided by an embodiment of the present disclosure.

FIG. 7 is a schematic diagram of an optional display interface provided by an embodiment of the present disclosure. In an embodiment of the present disclosure, by means of steps 201-205, different tissues of different patients may be performed with ultrasound detection and the object information, the scanning parameter information, the ultrasound image and the association may be stored. As shown in FIG. 7, it may include patient ID; ultrasound device information including device media access control address (MAC) and detecting position; and storage identifier including storage location and storage state. With the shown storage identifier, the storage location of a corresponding information may be determined as: local storage, or local server storage, or other cloud server storage. The storage state may include: success and failure; further, when the storage state is failure, an alarm message may be triggered or a secondary storage and backup may be automatically activated.

Figure 4:
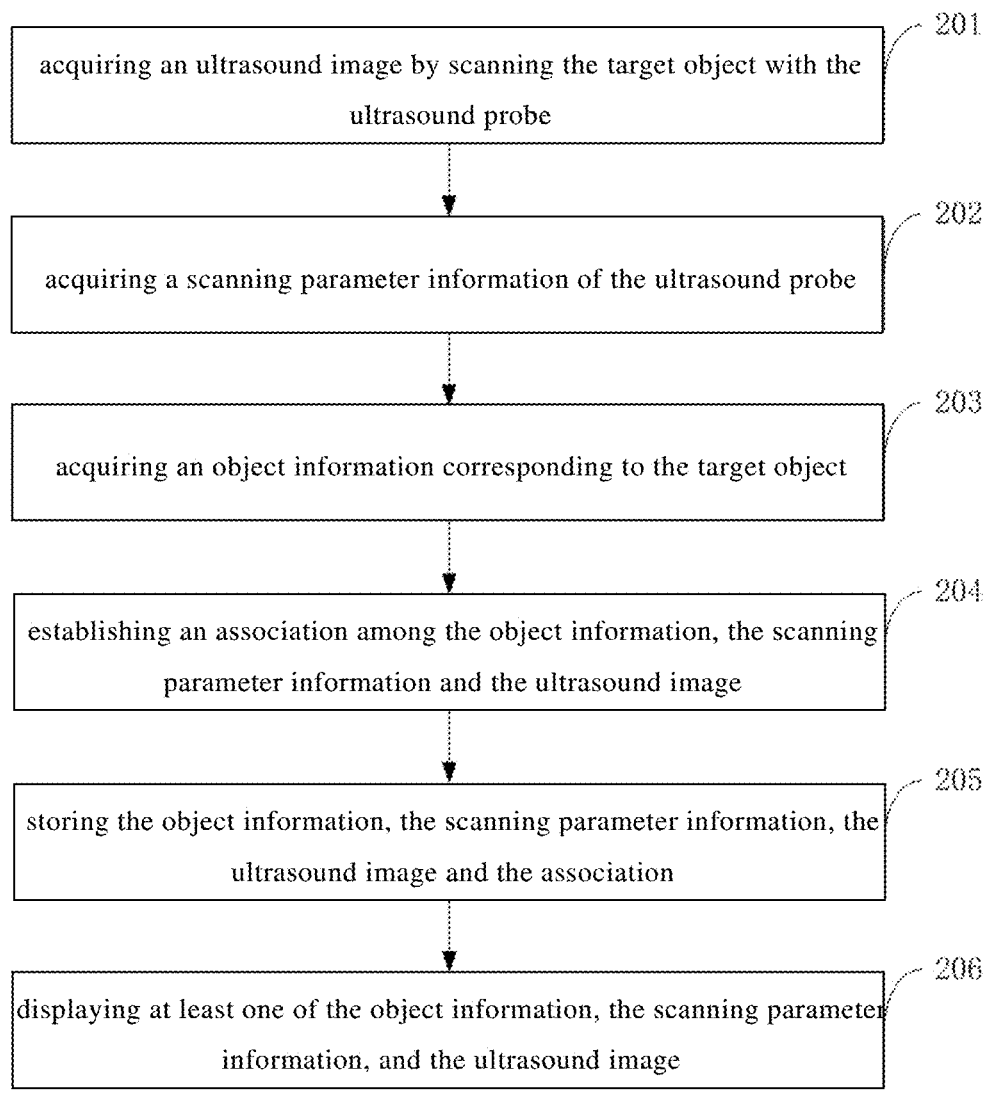
FIG. 4 is a schematic diagram of an optional flow of an ultrasonic data processing method provided by an embodiment of the present disclosure.

Further, as shown in FIG. 4, after step 205, the ultrasonic data processing method provided in the embodiment of the present disclosure may further include:

Step 206: displaying at least one of the object information, the scanning parameter information, and the ultrasound image.

In practice, different display instructions generated by human-computer interaction may display at least one of the object information, the scanning parameter information, and the ultrasound image via the ultrasound device. By the displayed object information, the scanning parameter information, and the ultrasound image, the user can clearly know that the ultrasound image is produced by the ultrasound device scanning on which target object at what time, and that the corresponding scanning parameters during scanning to realize the traceability of the scan.

In an embodiment of the present disclosure, the step of displaying the object information, the scanning parameter information and the ultrasound image may include:

outputting at least one of the object information, the scanning parameter information, and the ultrasound image according to at least one of a text, a graphic and a voice.

In an embodiment of the present disclosure, when receiving a human-machine interactive operating instruction to display the object information, the scanning parameter information and the ultrasound image, the corresponding information to be displayed currently can be displayed via the display 104 shown in FIG. 1; or, the object information and the scanning parameter information may be displayed by correspondingly specific graphic. The text or graphic may have a prompting function; for example, the text or graphic displayed on the screen may be in a highlighted state, to prompt the user to check, which is convenient for beginners to use. In particular, graphic elements may have dynamic effects, and thus have a high degree of recognition.

In an embodiment of the present disclosure, when receiving a human-computer interactive operating instruction to display the object information, the scanning parameter information and the ultrasound image, a speaker (not shown in the figure) of the ultrasound device shown in FIG. 1 may synchronously output the object information and the scanning parameter information corresponding to the displayed ultrasound image for the convenience of users.

Figure 8:
FIG. 8 is a schematic diagram of an optional display interface provided by an embodiment of the present disclosure.

FIG. 8 is a schematic diagram of an optional display interface provided by an embodiment of the present disclosure. In an embodiment of the present disclosure, by means of steps 201-206, the same part of a same patient may be performed with ultrasound detection in different chronological order, the object information, the scanning parameter information, the ultrasound image and the association may be stored, and the current ultrasound image may be displayed. As shown in FIG. 8, the scan location is fetus's nose and lip, and the display content may include ultrasound device name, MAC address, patient ID, examination sequence number, scan parameters, examination time, doctor's signature, and probe serial number used for each test.

Figure 9:
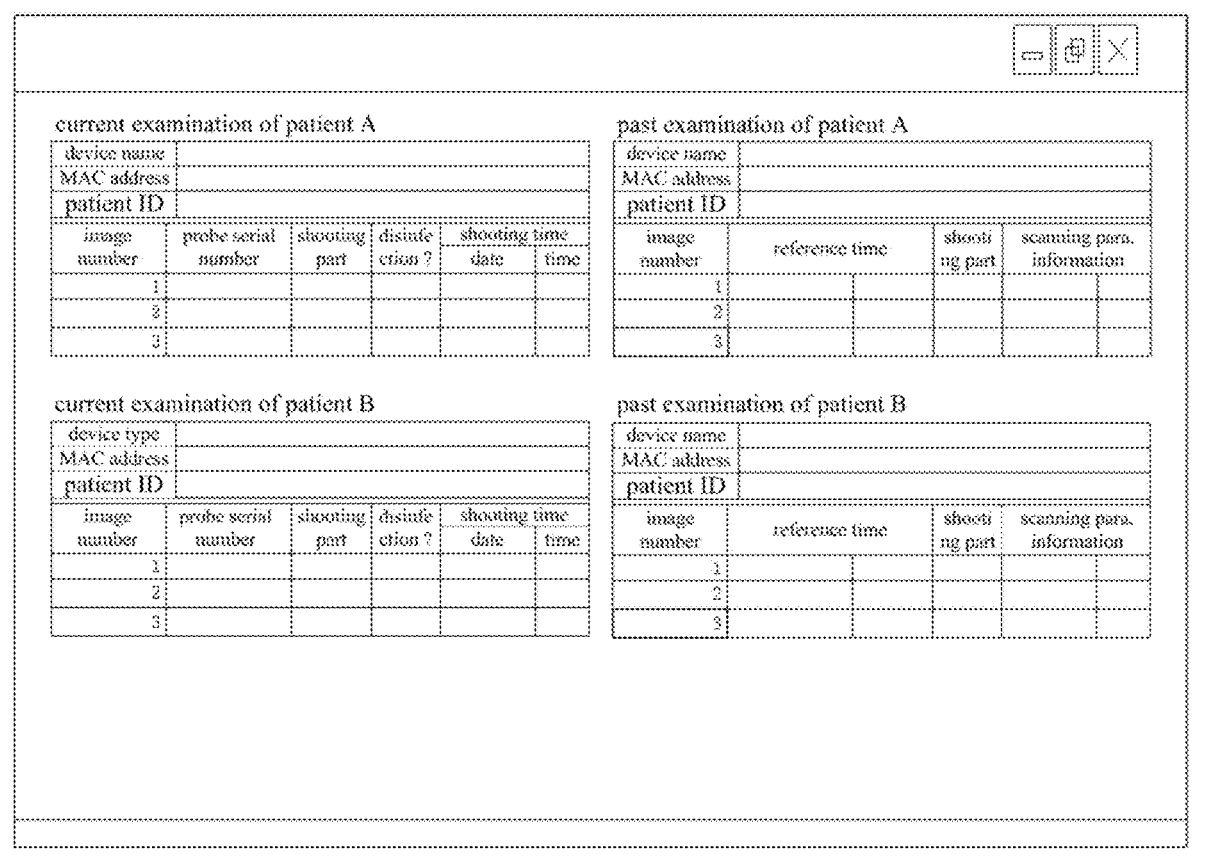

FIG. 9 is a schematic diagram of an optional display interface provided by an embodiment of the present disclosure. In an embodiment of the present disclosure, by means of steps 201-206, different parts of different patients may be performed with ultrasound detection in different chronological order, and the object information, the scanning parameter information, the ultrasound image and the association may be stored. As shown in FIG. 9, the ultrasound examinations of different patients A and B may be all displayed on the interface, and the display content may include ultrasound device name, MAC address, patient ID, ultrasound image number, scan parameters, shooting time, reference time, probe serial number and disinfection state corresponding to patient A, and ultrasound device name, MAC address, patient ID, ultrasound image number, scan parameters, shooting time, reference time, probe serial number and disinfection state corresponding to patient B.

The ultrasound image number may be used to retrieve an associated ultrasound image.

Figure 5:
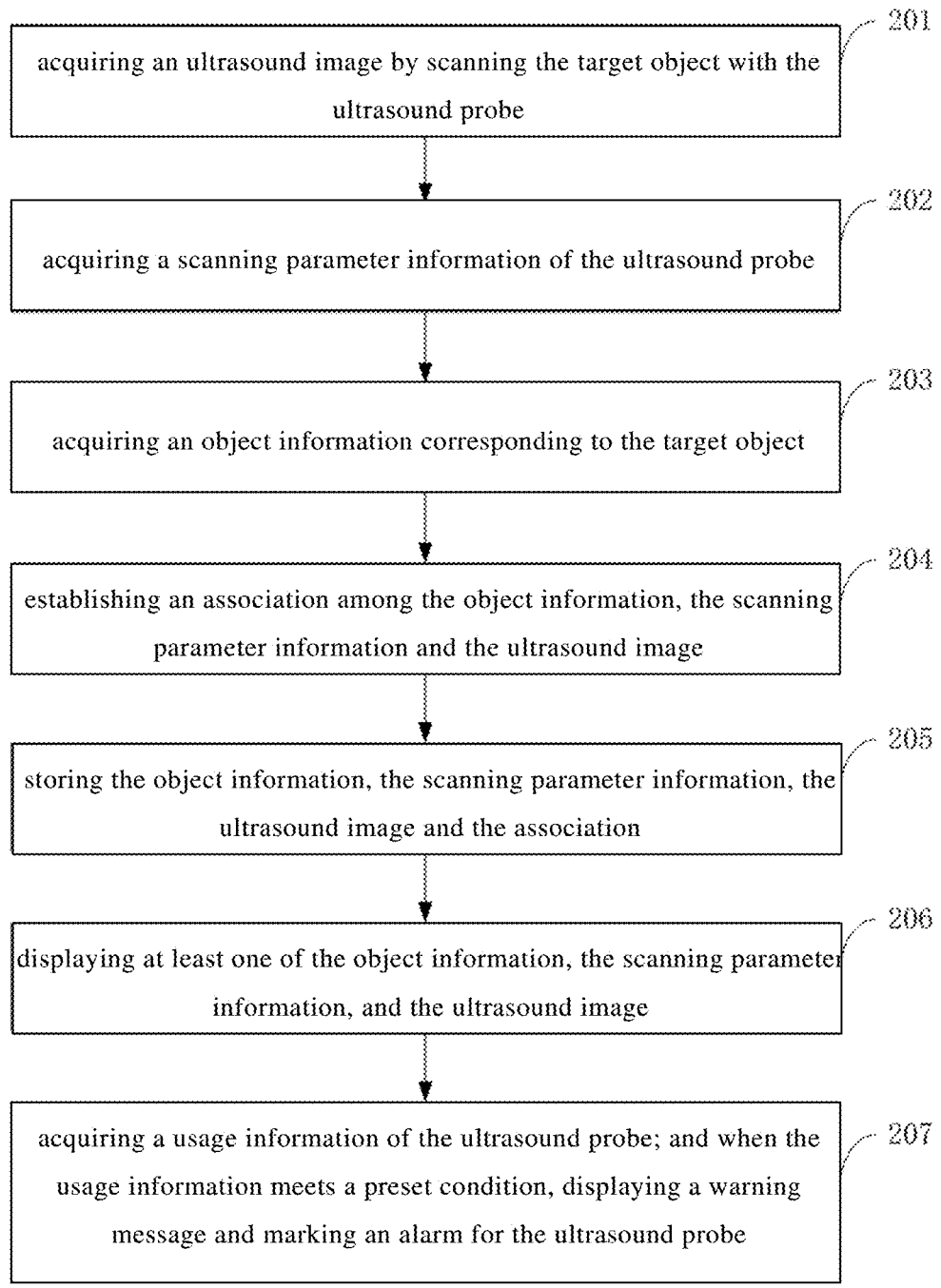
FIG. 5 is a schematic diagram of an optional flow of an ultrasonic data processing method provided by an embodiment of the present disclosure.

Further, as shown in FIG. 5, after step 206, the ultrasonic data processing method provided in the embodiment of the present disclosure may further include:

Step 207: acquiring a usage information of the ultrasound probe; and when the usage information meets a preset condition, displaying a warning message and marking an alarm for the ultrasound probe.

It can be seen that, the usage of each ultrasound probe can be detected when the probe of the ultrasound device is cross used, and a warning message may be sent out when the probe alarm parameter of the aggregate information for use of the ultrasound probe reaches an alarm threshold. For example, when the disease type of a target monitored by the ultrasound probe is contact-type cross-infection, a warning message may be displayed and an alarm may be marked for the ultrasound probe used. For another example, when the number of uses of the ultrasound probe is greater than a preset threshold, a warning message may be sent to prompt that the number of uses of the ultrasound probe has reached an upper limit, followed by disinfection or waste disposal, etc., which can be determined according to actual situation.

In an embodiment of the present disclosure, when an alarm marked for the used ultrasound probe is detected, a user can be prompted through the display screen of the ultrasound device to replace the ultrasound probe or perform disinfection treatment on the corresponding ultrasound probe.

Figure 10:
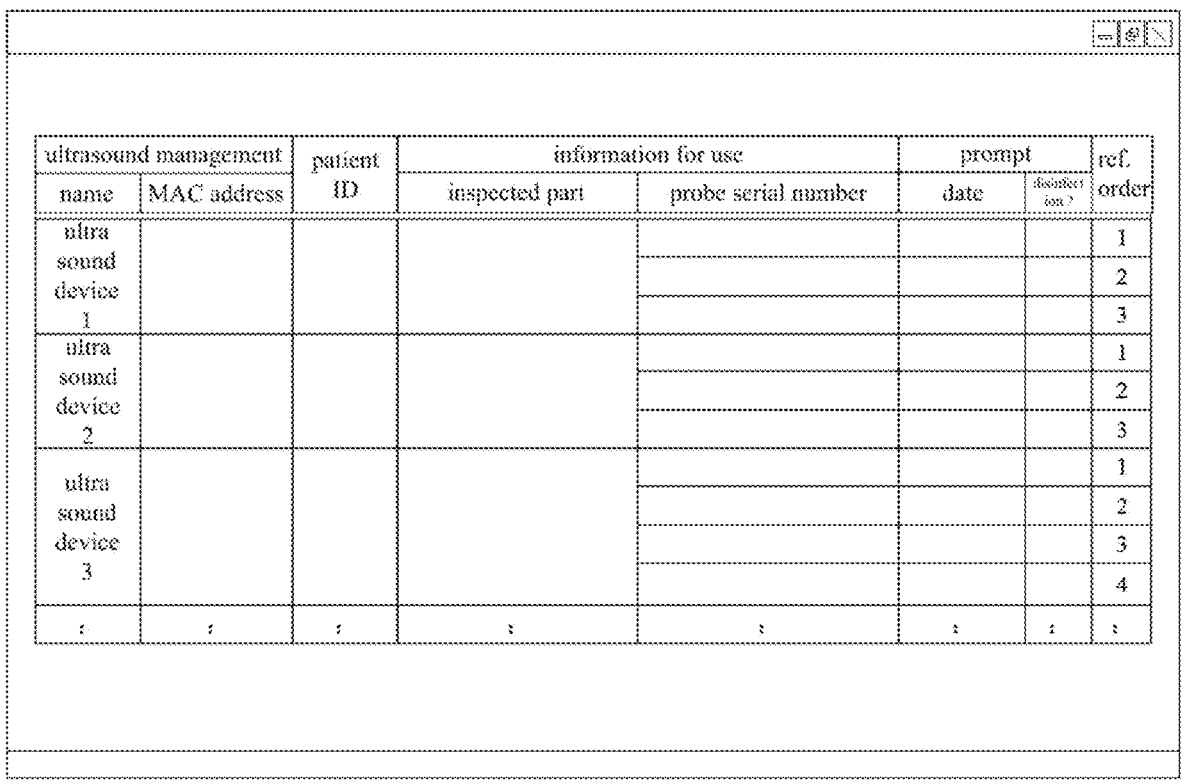
FIG. 10 is a schematic diagram of an optional display interface provided by an embodiment of the present disclosure.

FIG. 10 is a schematic diagram of an optional display interface provided by an embodiment of the present disclosure. In an embodiment of the present disclosure, by means of steps 201-207, different tissues of different patients may be performed with ultrasound detection. And for an ultrasonic testing department having a plurality of ultrasound devices, through the display interface shown in FIG. 10, you can acquire the number of different ultrasound devices and corresponding MAC addresses, the information of the inspected part and the probe serial number used, and examination date and whether it is necessary to perform disinfection on the used ultrasound probe.

Those skilled in the art may understand that the embodiments of the present disclosure may be provided as methods, systems, or computer program products. Therefore, the embodiments of the present disclosure may adopt in the form of hardware, software, or combination thereof. Moreover, the embodiments of the present disclosure may adopt the form of a computer program product implemented on one or more computer-usable storage media (including disk storage, optical storage, etc.) containing computer-usable program codes.

The embodiments of the present disclosure may be described with reference to the methods, devices (systems), and flowcharts and/or block diagrams of the computer program products according to the embodiments of the present disclosure. It should be understood that each process and/or block and/or the combination thereof in the flowcharts and/or block diagrams can be realized by computer procedure operations. These computer procedure operations can be provided on the processor of a general-purpose computer, special-purpose computer, embedded processor, or other programmable data processing apparatus to generate a machine, so that the operations performed by the processor of the computer or other programmable data processing apparatus can produce means for realizing the functions specified in a flow or multiple flows in the flowchart and/or a block or multiple blocks in the block diagram.

These computer procedure operations may also be stored in a computer-readable memory that can guide a computer or other programmable data processing apparatus to work in a specific manner, so that the operations stored in the computer-readable memory may produce manufactures including an operating device that may implement the functions specified in a flow or multiple flows in the flowchart and/or a block or multiple blocks in the block diagram.

These computer procedure operations may also be loaded on a computer or other programmable data processing apparatus, so that a series of operating steps may be executed on the computer or other programmable apparatus to produce computer-implemented processing; thus steps for realizing the functions specified in a flow or multiple flows in the flowchart and/or a block or multiple blocks in the block diagram may be provided on the computer or other programmable apparatus.

The above may only describe preferred embodiments of the present disclosure and do not limit the scope of protection of the present disclosure. Any modification, equivalent replacement and improvement made within the spirit and principle of the present disclosure shall be included within the scope of protection of the present disclosure.

The invention claimed is:

1. An ultrasonic data processing method applied to an ultrasound device, comprising:
    acquiring an ultrasound image by scanning a target object with an ultrasound probe;
    acquiring probe attribute information of the ultrasound probe, the probe attribute information at least comprising a probe serial number;
    acquiring object information corresponding to the target object; and
    establishing an association among the object information, the probe attribute information, and the ultrasound image, so as to allow a medical staff to trace use records of the ultrasound probe in subsequent operations.

2. The method according to claim 1, further comprising:
    storing the object information, the probe attribute information, the ultrasound image, and the association.

3. The method according to claim 2, further comprising:
    after storing the object information, the probe attribute information, the ultrasound image, and the association, acquiring a storage identifier of the object information, the probe attribute information, the ultrasound image, and the association, wherein the storage identifier represents a storage state and a storage location of the object information, the probe attribute information, the ultrasound image, and the association.

4. The method according to claim 1, further comprising:
    displaying at least one of the object information, the probe attribute information and the ultrasound image.

5. The method according to claim 4, wherein displaying at least one of the object information, the probe attribute information, and the ultrasound image comprises:
    displaying at least one of the object information, the probe attribute information and the ultrasound image by at least one of a text, a graphic, and a voice.

6. The method according to claim 1, wherein acquiring the probe attribute information of the ultrasound probe comprises:
    monitoring the ultrasound probe; and
    reading the probe attribute information when the ultrasound probe is activated.

7. The method according to claim 1, wherein acquiring the probe attribute information of the ultrasound probe comprises:
    receiving a notification sent by the ultrasound probe, the notification representing that the ultrasound probe is activated; and
    in response to the notification, receiving the probe attribute information sent by the ultrasound probe.

8. The method according to claim 1, further comprising:
    acquiring usage information of the ultrasound probe; and
    when the usage information meets a present condition, displaying a warning message or marking an alarm for the ultrasound probe.

9. The method according to claim 1, wherein the object information comprises at least one of object information of the target object and object information of a scanner who scans the target object.

10. The method according to claim 1, wherein the probe attribute information further comprises a probe type.

11. The method according to claim 1, wherein the probe attribute information is the probe serial number, and acquiring the probe attribute information of the ultrasound probe comprises:
    acquiring the probe serial number from the ultrasound probe; or
    receiving an input for the probe serial number, and acquiring the probe serial number according to the input; or
    acquiring the probe serial number from a local memory.

12. The method according to claim 1, wherein the probe serial number is stored in a memory chip of the ultrasound probe, or fixed on the ultrasound probe in a manner of firmware.

13. The method according to claim 1, wherein establishing the association among the object information, the probe attribute information and the ultrasound image comprises:
    establishing an association among the object information, the probe serial number, and an ultrasound image number.

14. An ultrasound device, comprising:
    an ultrasound probe configured to scan a target object to acquire an ultrasound image;
    a memory configured to store executable instructions; and
    a processor configured to execute the executable instructions stored in the memory to:
        acquire the ultrasound image by scanning the target object with the ultrasound probe;
        acquire probe attribute information of the ultrasound probe, the probe attribute information at least comprising a probe serial number;
        acquire object information corresponding to the target object; and
        establish an association among the object information, the probe attribute information, and the ultrasound image, so as to allow a medical staff to trace use records of the ultrasound probe in subsequent operations.

15. The ultrasound device according to claim 14, wherein the memory is further configured to store the object information, the probe attribute information, the ultrasound image, and the association.

16. The ultrasound device according to claim 15, wherein the processor is further configured to acquire a storage identifier of the object information, the probe attribute information, the ultrasound image, and the association, wherein the storage identifier represents a storage state and a storage location of the object information, the probe attribute information, the ultrasound image, and the association.

17. The ultrasound device according to claim 14, further comprising:
    a display configured to display at least one of the object information, the probe attribute information, and the ultrasound image.

18. The ultrasound device according to claim 17, wherein the display is further configured to display at least one of the object information, the probe attribute information, and the ultrasound image by at least one of a text, a graphic, and a voice.

19. The ultrasound device according to claim 14, wherein the processor is further configured to:
    monitor the ultrasound probe, and read the probe attribute information when the ultrasound probe is activated; or
    receive a notification sent by the ultrasound probe, the notification representing that the ultrasound probe is activated, and in response to the notification, receive the probe attribute information sent by the ultrasound probe.

20. The ultrasound device according to claim 14, wherein the processor is further configured to acquire usage information of the ultrasound probe; and
    the ultrasound device further comprises:
    a display configured to display a warning message or mark an alarm for the ultrasound probe.

21. The ultrasound device according to claim 14, wherein the object information comprises at least one of object information of the target object and object information of a scanner who scans the target object.

22. The ultrasound device according to claim 14, wherein the probe attribute information further comprises a probe type.

* * * * *